(12) United States Patent
Lyon et al.

(10) Patent No.: US 6,573,737 B1
(45) Date of Patent: Jun. 3, 2003

(54) METHOD AND APPARATUS FOR NON-CONTACT MEASUREMENT OF ELECTRICAL PROPERTIES OF MATERIALS

(75) Inventors: Stephen A. Lyon, Cranbury, NJ (US); Eric A. Shaner, Princeton, NJ (US); Igor E. Trofimov, Long Vallley, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 09/803,650

(22) Filed: Mar. 9, 2001

Related U.S. Application Data

(60) Provisional application No. 60/188,538, filed on Mar. 10, 2000.

(51) Int. Cl.[7] .............................................. G01R 31/308
(52) U.S. Cl. ....................................... 324/753; 324/752
(58) Field of Search ................................ 324/752, 753, 324/754, 96; 356/484, 901.1, 432, 445

(56) References Cited

U.S. PATENT DOCUMENTS

| | | | | |
|---|---|---|---|---|
| 4,910,458 A | * | 3/1990 | Forsyth et al. | 324/753 |
| 5,051,804 A | * | 9/1991 | Morse et al. | 257/185 |
| 5,706,094 A | * | 1/1998 | Maris | 356/432 |
| 5,757,503 A | * | 5/1998 | Brady et al. | 250/559.3 |
| 5,933,555 A | * | 8/1999 | Shen | 385/11 |

OTHER PUBLICATIONS

Hasnain, et al., "Effect of Optical Phonons on Femtosecond Pulse Propagation in Coplanar Striplines," App. Phys. Lett. 56, 515 (1990).

Shaner, et al., "Coplanar Striplines on Flexible Low Dielectric Constant Substrates," Abstract Submitted for the MAR99 Meeting of The American Physical Society.

Shaner, et al., Coplanar Striplines on Flexible Low Dielectric Constant Substrates, presentation to American Physical Society Centennial Meeting Program, Mar. 26, 1999.

* cited by examiner

Primary Examiner—Kamand Cuneo
Assistant Examiner—Tung X. Nguyen
(74) Attorney, Agent, or Firm—Wolff & Samson

(57) ABSTRACT

The present invention relates to a method and apparatus for measuring material properties using guided-wave THz spectroscopy to measure the complex dielectric functions of materials. A high frequency wave is created and launched along a waveguide positioned in close proximity to a material under test. The wave is sampled initially, allowed to propagate, and sampled again. The samples are processed to derive information, such as resistivity, of the wafer. The method and apparatus of the present invention not only allows one to obtain information about the DC conductivity of metals, but also provides information about the high frequency behavior of materials—metals, and dielectrics as well—which is becoming particularly useful at the time when processor clocks are running at frequencies approaching GHz levels. The present invention provides for non-contact, non-destructive, non-contaminating testing.

53 Claims, 19 Drawing Sheets

$N_{eff} = \sqrt{\varepsilon_{eff}}$ VS FREQUENCY

END REFLECTIONS

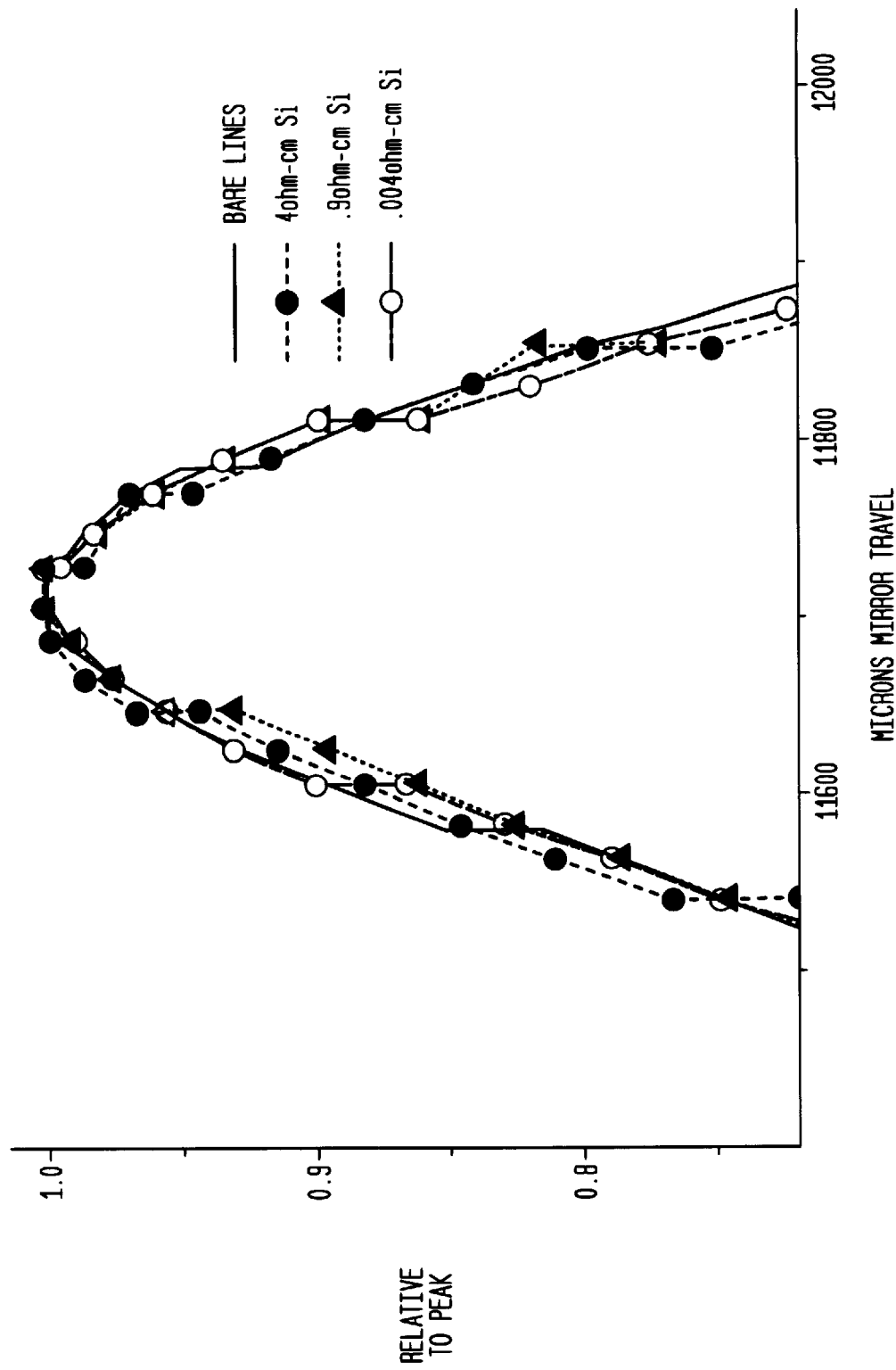

ALPHA VS. FREQUENCY

END REFLECTION

END REFLECTION

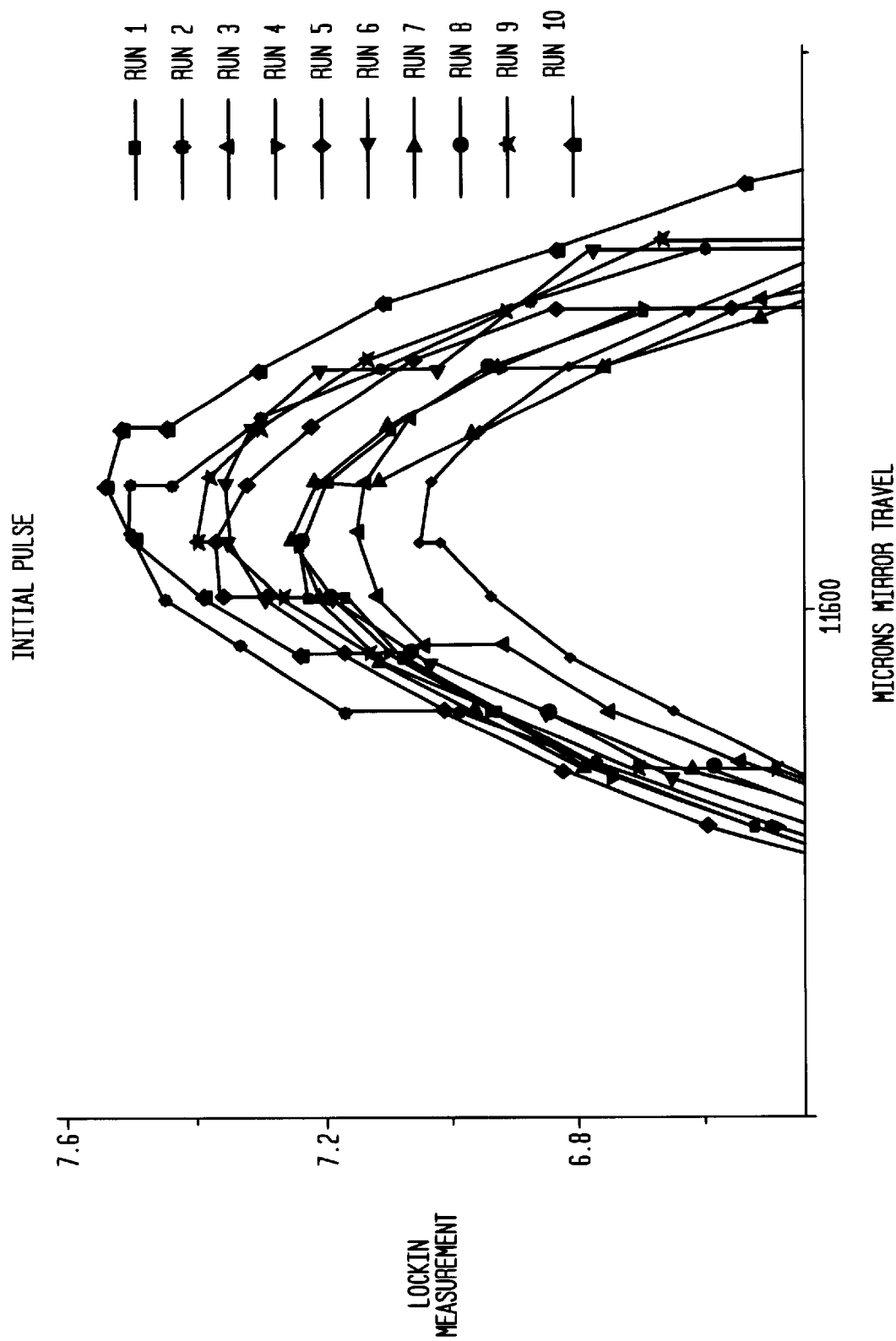

METHOD AND APPARATUS FOR NON-CONTACT MEASUREMENT OF ELECTRICAL PROPERTIES OF MATERIALS

RELATED APPLICATIONS

The present invention is related to and claims the benefit of U.S. Provisional Patent Application Ser. No. 60/188,538, filed Mar. 10, 2000 and entitled "High Frequency Guided-Wave Proximity Probe of Electrical Properties of Materials", which provisional application is assigned to the same assignee and is incorporated by reference herein.

GOVERNMENT RIGHTS

The present invention has been made under federal grant no. DAAL 03-92-G-0146, and the government may have certain rights to the subject invention.

BACKGROUND OF THE INVENTION

1. Field of the Invention

The present invention relates to a method and apparatus for material metrology without contacting, destroying, or contaminating the material under test (MUT), using a high frequency probe. More specifically, the present invention relates to guided-wave GigaHertz (GHz) and Tera-Hertz (THz) spectroscopy for measuring material properties such as resistivity and dielectric response function ($\in(\omega)$).

2. Related Art

The conventional method in the semiconductor industry for measuring the sheet resistance of wafers and thin films is based on so-called "4-point probe." The measurements involve direct contact of electrodes with the semiconductor wafer, rendering it useless for further processing. Thus, dummy wafers must be run through the various processing steps in order to calibrate the technological process.

OBJECTS AND SUMMARY OF THE INVENTION

It is a primary object of the present invention to provide a non-destructive probe for material metrology.

It is a further object of the present invention to provide a non-contact probe for material metrology.

It is a further object of the present invention to provide a non-contaminating probe for material metrology.

It is a further object of the present invention to provide method for measuring the resistivity of a material without destroying, without contacting, and without contaminating the material under testing (MUT).

It is another object of the present invention to provide probe for material metrology in the form of a waveguide which is placed adjacent to a MUT.

It is even an additional object of the present invention to provide a material metrology probe which operates into the Tera Hertz (THz) frequency range.

The present invention relates to a method and apparatus for material metrology (e.g., measurement of the complex conductivity of the material) as a function of a response to guided-wave GHz and THz signals. A high frequency wave is created and launched along a waveguide positioned in close proximity to an MUT. The wave is sampled initially, allowed to interact with the material, and sampled again. The samples are processed to derive information, such as resistivity or dielectric response function, of the material. The method and apparatus of the invention not only allows one to obtain information about the DC conductivity of metals, but also provides information about the high frequency behavior of materials—both metals and dielectrics—which is becoming particularly useful at the time when processor clocks are running at frequencies exceeding GHz levels. The present invention provides for non-contact, non-destructive, and non-contaminating testing.

BRIEF DESCRIPTION OF THE DRAWINGS

Other important objects and features of the invention will be apparent from the following Detailed Description of the Invention taken in connection with the accompanying drawing, in which:

FIGS. 6a, 6b and 6c are graphs of a time-domain spectra taken for three Si samples of different doping.

FIG. 11 is a graph showing the changes in the amplitude and position of the reference peak during static repeatability test.

DETAILED DESCRIPTION OF THE INVENTION

A new device and methodology for non-destructive, non-contact metrology of conductive and semi-conductive materials is disclosed and described herein. The invention operates to effect an interaction between a pulsed electric field and a material under test (MUT), followed by a determination of changes in the electric field pulses resulting from the interaction. The electric field pulse changes are then translated into parameter values for the MUT.

In particular, a pulsed electric field in the microwave (GHz-THz) frequency range is caused to propagate in a wave guide placed in proximity to a given MUT, and the field is then sampled at another point in the waveguide, after having interacted with the MUT. The laser pulses create electrical pulses, which probe the material under test, and then the electrical pulses are measured by a second laser pulse and suitable electronics. The MUT is brought into close proximity to the waveguide. The electrical pulses are attenuated and their shape is changed by their interaction with the MUT. From these changes in the electrical pulse, the electrical properties of the material can be deduced.

In a preferred embodiment of the invention, the waveguide of the invention is implemented as a coplanar strip transmission line (CPS) deposited on a photoconducting substrate. As is known, excitation of such a CPS by a pulsed laser source operates to generate a corresponding pulsed electrical field in the transmission line. In order to minimize dispersion of the electrical pulse due to interaction with the waveguide, it is preferable that the CPS be operated in a quasi TEM mode.

Figure 1A:
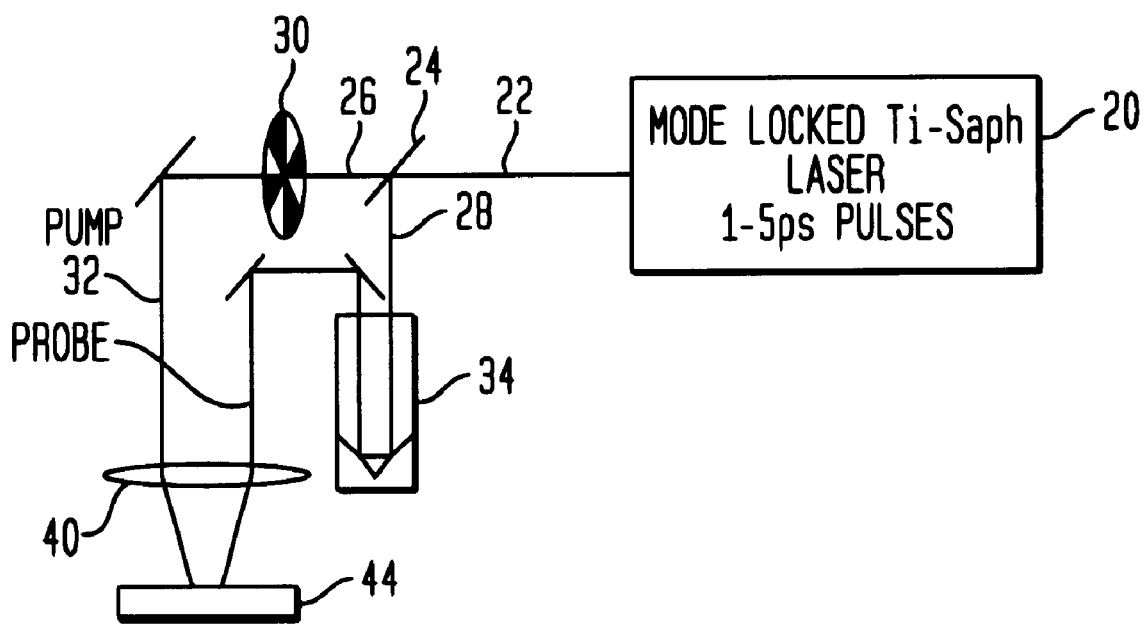
FIG. 1(a) is a schematic diagram of an illustrative apparatus for carrying out the methodology of the invention.

An over all schematic depiction of an illustrative apparatus for carrying out the invention is shown in FIG. 1a. With reference to that figure, a laser-based pump-probe 20, such as Ti: Sapphire (Tsunami, Spectra-Physics) with an ion-laser pump, operates to generate short pulses of 800 nm laser light 22—for the illustrative embodiment, typical pulse duration is in the 2–3 psec range. Light pulses 22 are split by splitter 24 into two beams, a pump beam 26 and a probe beam 28 of equal intensity (5–10 mW). A mechanical chopper 30 operating, illustratively, at 1 kHz is used to create modulated pump beam 32. The probe beam 28 is sent through a delay stage 34 that controls the relative delay of the probe (or sampling) pulse with respect to the pump beam. The pump and probe beams are focused by the microscope lens 40 onto the launching and sampling gaps of the sampling head 44. The sampling head 44 will include a generator for converting the light pulses into Giga-Hertz (GHz) or Tera-Hertz (THz) bandwidth electrical pulses and a guided wave structure for delivering an electrical pulse from a point of generation to a sampling position.

Figure 1B:
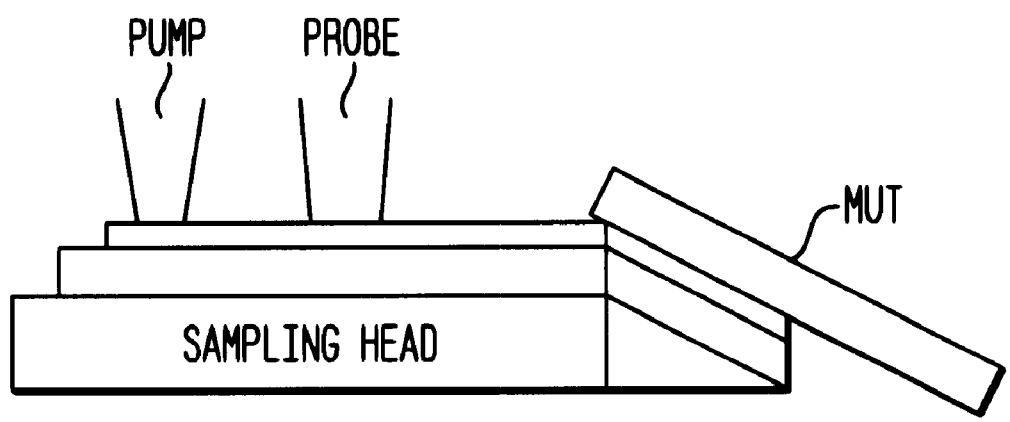
FIG. 1(b) is an enlarged schematic view of the sampling head thereof.

An enlarged schematic view of the sampling head is shown in FIG. 1b. It is to be noted in the figure that the a MUT is disposed adjacent to an angular offset portion of the sampling head. This configuration represents a preferred embodiment of the invention, and will be explained in more detail below.

Figure 2A:
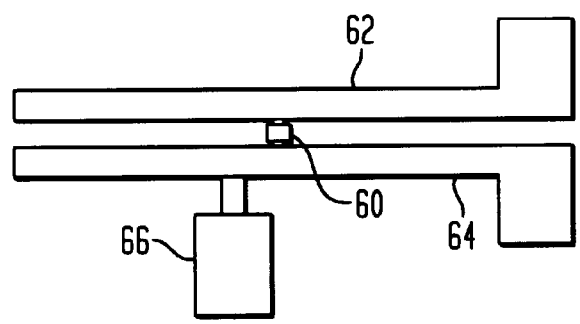
FIG. 2a is a schematic diagram of a coplanar strip waveguide.

In the preferred embodiment, the generator and guided wave structure are embodied as a coplanar transmission line on a surface of a substrate of photoconductive material, as depicted in FIG. 2a. In the figure, the coplanar transmission lines are indicated by reference designators 62 and 64 and the point of impingement of the optical pulses on the substrate is indicated at 60. The electrical signal from the sampling head 66 is amplified, synchronously detected by a lock-in amplifier, digitized, and stored as the delay stage is scanned. This technique time resolves pulse transport along the waveguide. The data can be post-processed to extract material parameters of interest.

Other field-generation/sampling arrangements for effecting and measuring interaction of the field with an MUT, according to the method of the invention, will be known to those skilled in the art and are intended to be encompassed within the scope of the invention as described and claimed herein.

Figure 2B:
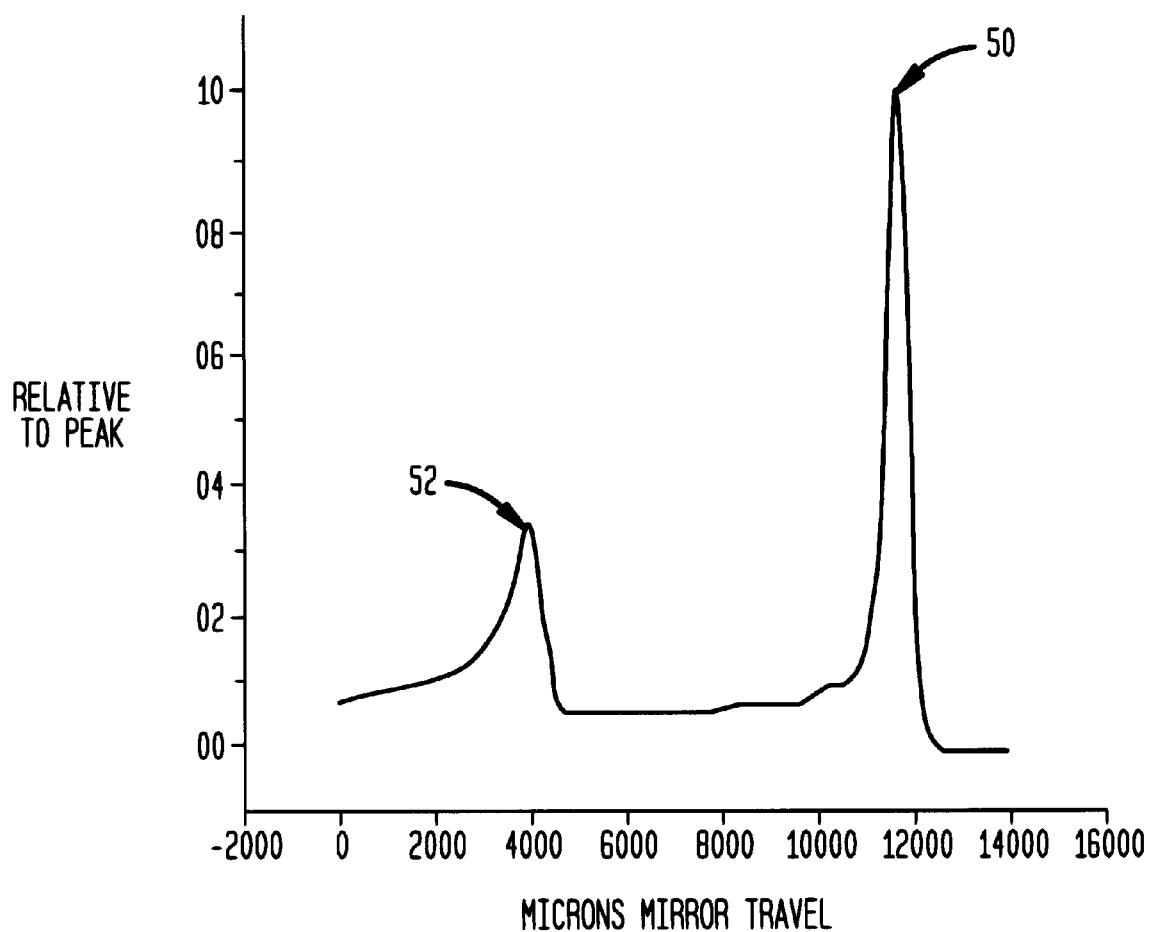
FIG. 2b is a graph of the typical response thereof.

An example of recorded data using the device of FIGS. 1a, 1b and 2a is shown in the graph of FIG. 2b where mirror travel (probe delay) in microns is plotted against signal amplitude (data normalized to peak). The sharp peak 50 at 12000 microns is the pulse shape detected at sampling head 66 when the pulse is on its way from the launching gap (the spot 60 between lines 62 and 64 in FIG. 2a). The second peak 52 at about 4000 microns represents the pulse that has reflected from the end of the waveguide and returned back to the sampling point 66. One can see that both the amplitude and the shape of the second peak differ substantially from the first one. These changes are due to dispersion in the waveguide itself, and from reflection losses at the end of the waveguide. Electrical properties of the MUT contribute to the net dielectric function, $\in(\omega)$, of the waveguide (characterized by $n(\omega)$ and $\alpha(\omega)$). As such, these properties can be extracted through analysis of pulse propagation on the waveguide as will be detailed in the following sections.

As a predicate to a detailed discussion of the operation of the invention, it is useful to briefly consider certain facets of waveguide propagation, particularly as related to coplanar transmission lines. The change of shape of an electrical pulse on a transmission line after propagating a distance x is described in the frequency domain by:

$$v(x, \omega) = v(0, \omega)\exp\left\{-\alpha(\omega)x + i\frac{\omega}{c}n(\omega)x\right\} \quad (1)$$

where $v(x,\omega)$ and $v(0,\omega)$ are the Fourier transforms of the input and propagated pulse respectively; $\alpha(\omega)$ the attenuation constant of the transmission line, and $n(\omega)$ the effective index of refraction that an electrical pulse sees on the transmission line structure. $\alpha(\omega)$ and $n(\omega)$ are determined from the experimental input and output waveforms as:

$$\alpha(\omega) = \frac{1}{x} \cdot \ln\left\{\frac{|v(x, \omega)|}{|v(0, \omega)|}\right\} \quad (2)$$

$$n(\omega) = \frac{c}{\omega x} \cdot \arg\left\{\frac{v(0, \omega)}{v(x, \omega)}\right\} \quad (3)$$

Figure 4:
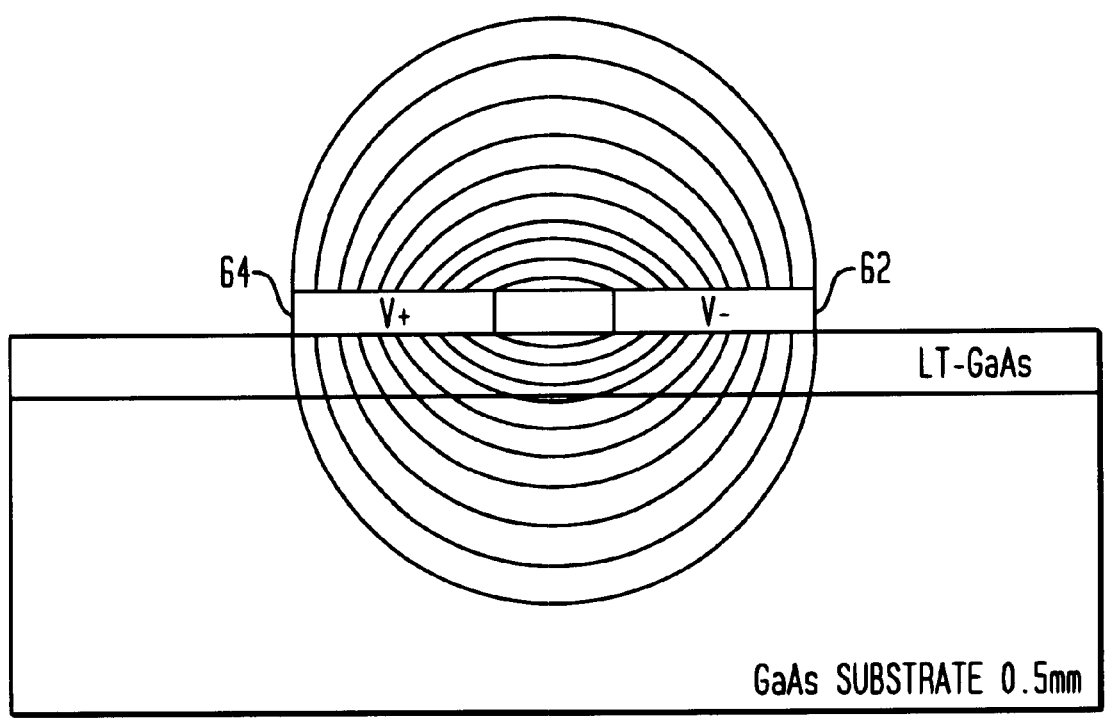
FIG. 4 is a schematic diagram of the coplanar strip line according to the present invention.

It should be noted that fringing electric fields from the transmission lines will extend partially into the substrate region for the transmission lines, as well as into the air above those lines, as shown in FIG. 4. Similarly, when an MUT is disposed proximally to the plane of the transmission line (herein characterized as a "superstrate"), those fringing electric fields lines will extend into, and interact with the MUT. In the same vein, note that $\alpha(\omega)$ and $n(\omega)$ differ from the corresponding values of substrate $\alpha_{Sub}(\omega)$, $\in_{Sub}(\omega)$ and superstrate $\alpha_{Super}(\omega)$, $\in_{Super}(\omega)$, and that the conductors of the strip lines 62 and 64 also contribute to the impedance of the transmission line. For simplicity, the effects of the superstrate will be omitted from the basic analysis to follow. However, it should be noted that Equations 2 and 3 are valid for waveguides in general.

A number of factors affect electrical pulse propagation along a transmission line. Because, as noted above, electric fields partially extend into the air (or the superstrate) above the substrate, the effective dielectric constant $\in_{eff}$ of the line at low frequencies—i.e., at wavelengths much longer than the width of the line—has a value between that of the air/superstrate and the substrate material. The $\in_{eff}$ is determined by the percentage of the waveguide mode that protrudes into both. In the absence of a superstrate, this percentage decreases with increasing frequency until almost the entire mode propagates in the substrate material. This leads to modal dispersion: the high frequency components of the ultra-short (therefore broad-band) electrical pulse propagate at a slower phase velocity than lower frequencies, causing broadening of the pulse in the time domain. The dispersion relations of coplanar lines, in the absence of a superstrate, can be approximated over a wide range of parameters with the following expression:

$$\sqrt{\varepsilon_{\mathit{eff}}(\omega)} = \sqrt{\varepsilon_{\mathit{eff}}(0)} + \frac{\sqrt{\varepsilon_{\mathit{Sub}}} - \sqrt{\varepsilon_{\mathit{eff}}(0)}}{1 + (\omega_{\mathit{disp}}/\omega)^{1.8}} \quad (6)$$

where $$\omega_{TE} = \frac{\pi c}{2t\sqrt{\varepsilon_{\mathit{Sub}} - 1}}$$

is the transverse electric mode cutoff frequency and $$\log\left(\frac{\omega_{\mathit{disp}}}{\omega_{TE}}\right) = \frac{1}{2}\left(\sqrt{q^2 + .14} - q\right) \text{ where } q = \log\left(\frac{s}{t}\right).$$

c—the velocity of light, t—substrate thickness. The static effective index is given by:

$$\sqrt{\varepsilon_{\mathit{eff}}(0)} = 1 + \frac{\sqrt{1/2(1+\varepsilon_{\mathit{Sub}})} - 1}{[1 + (s/t)^{1.95}]^{0.37}} \quad (7)$$

with s being line spacing.

Figure 3:
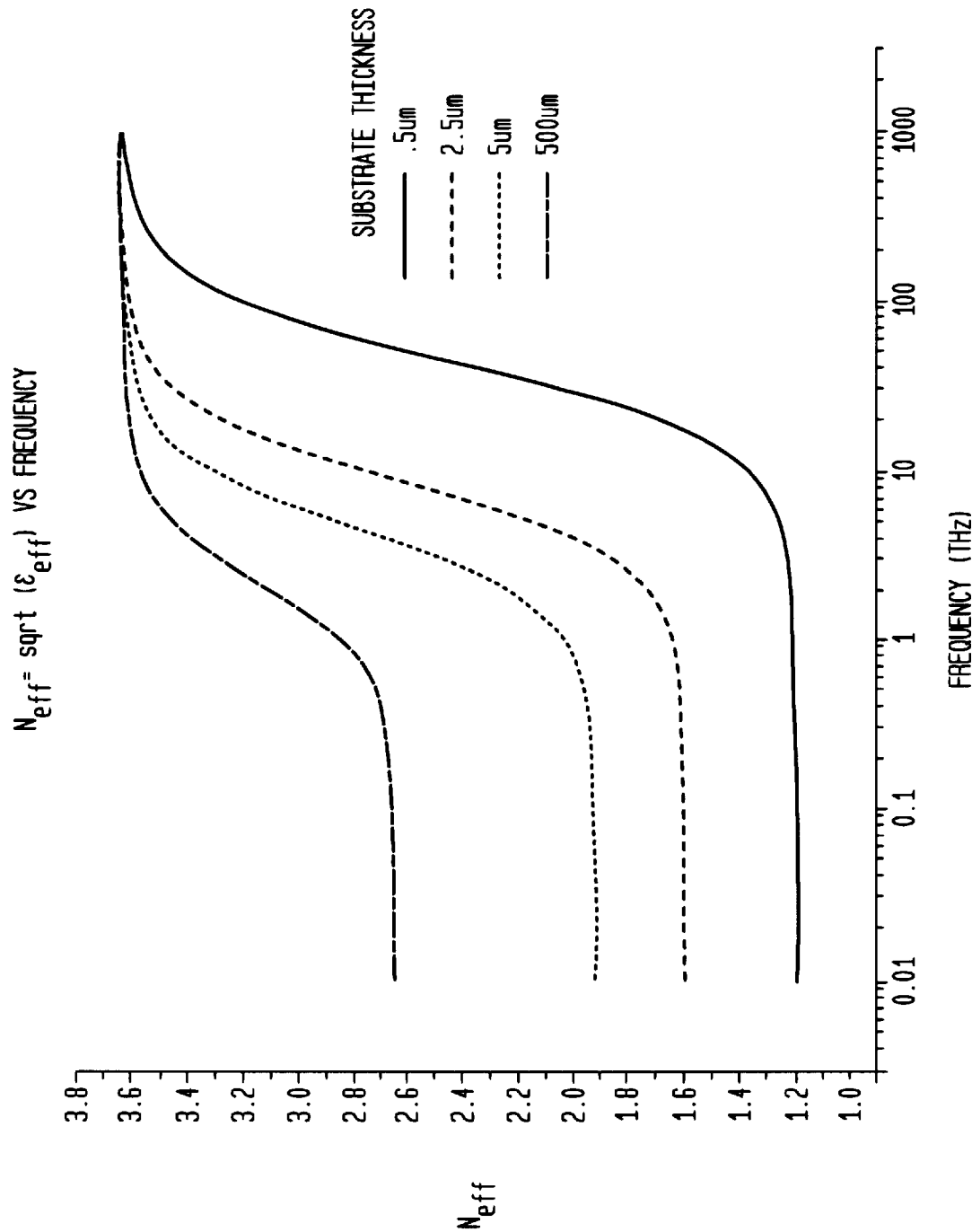
FIG. 3 is a graph of effective index versus frequency for coplanar strips on GaAs substrates of various thickness.

The dispersion curves for a coplanar stripline, again in the absence of superstrate, with 10 µm strip/slot width are shown in FIG. 3. These dispersion curves demonstrate that by decreasing the thickness of the substrate, and/or by using a substrate with low index of refraction the dispersion frequency can be increased substantially, effectively eliminating the effect of modal dispersion of coplanar lines on short pulse propagation.

Short pulses can be distorted by material dispersion, which is particularly important near dielectric resonances e.g. optical phonons. The frequency dependence of the dielectric constant is given by:

$$\varepsilon_{\mathit{Sub}} = \varepsilon_{\infty} + \frac{f_{TO}^2(\varepsilon_0 - \varepsilon_{\infty})}{f_{TO}^2 - f^2 + i\gamma_p f} \quad (8)$$

where $\varepsilon_0$ and $\varepsilon_{\infty}$ are static and optical dielectric constant, $f_{TO}$ is the resonant phonon frequency, and $\gamma_p$ is a phonon damping coefficient. For GaAs: $\varepsilon_0$=13.1, $\varepsilon_{\infty}$=10.9, $f_{TO}$=8.032 THz, and $\gamma_p$=60.48 GHz. It has been shown by Hasnain, et al., "Effect of Optical Phonons on Femtosecond Pulse Propagation in Coplanar Striplines" Appl. Phys. Lett. 56, 515 (1990) that, similar to the case of modal dispersion, the use of ultrathin substrates can dramatically reduce the effect of material dispersion on electrical pulse propagation.

Another source of loss is dispersion and absorption caused by the material of the transmission line conductors. The conductor surface impedance is given by:

$$Z_s(\omega) = \frac{1+i}{\sigma\delta}\coth\left[\frac{t(1+i)}{\delta}\right] \quad (9)$$

where σ is the conductivity, and the skin depth $$\delta = \sqrt{\frac{2}{\omega\sigma\mu_0}}.$$

For normal metals σ is real for the frequencies below 100 THz, thus leading to resistive skin-effect losses as a dominant effect.

Coplanar striplines also suffer from radiation losses. Because the propagation speed of the electrical pulse on the line is higher than the phase velocity of light in the substrate at the same frequency, the pulse is losing energy to the Cherenkov type radiation into the substrate. The corresponding propagation coefficient is given by the formula (see Frankel, IEEE TMTT, 39, N06, 91, pg 910):

$$\alpha_{\mathrm{rad}}(\omega) = \pi^5 \frac{(3-\sqrt{8})}{2}\sqrt{\frac{\varepsilon_{\mathit{eff}}(\omega)}{\varepsilon_{\mathit{Sub}}}}\left(1 - \frac{\varepsilon_{\mathit{eff}}(\omega)}{\varepsilon_{\mathit{Sub}}}\right)^2 \left[\frac{(S+2W)^2 \varepsilon_{\mathit{Sub}}^{3/2}}{\lambda^3 K'(k)K(k)}\right] \quad (10)$$

where W is the width of the transmission line, S is the spacing between the lines, λ is the wavelength of the radiation in the substrate, and K'(k) and K(k) are elliptic integrals, respectively. Because $\alpha_{\mathrm{rad}}(\omega)$ is increasing with frequency as $\omega^3$, for sub-picosecond pulses the radiation losses can dominate all other mechanisms for certain waveguide designs.

Taking into account all of the heretofore described loss mechanisms, one can rewrite the effective attenuation and index equations (2,3) for the case of no superstrate, small losses and shunt conductances as follows:

$$\alpha(\omega) = \alpha_{\mathit{Sub}}(\omega) + \alpha_{\mathrm{rad}}(\omega) + \frac{\sqrt{\varepsilon_{\mathit{eff}}(\omega)}}{120\cdot\pi}\mathrm{Re}[Z_s(\omega)]\frac{g_2}{g_1} \quad (11)$$

and $$n(\omega) = \sqrt{\varepsilon_{\mathit{eff}}(\omega)}\left[1 + \frac{\mathrm{Im}[Z_s(\omega)]}{\omega\mu_0}\frac{g_2}{g_1}\right] \quad (12)$$

where $g_1$ and $g_2$ depend on waveguide geometry. It is to be understood that the MUT will make its own contribution to n(ω) and α(ω). However, equations 2 and 3 still remain valid. Closed form expressions for arbitrary MUT (superstrate) are difficult to create. As such, numerical modeling will most likely be necessary in order to calculate the contribution a given MUT will make to n(ω) and α(ω).

Figure 5A:
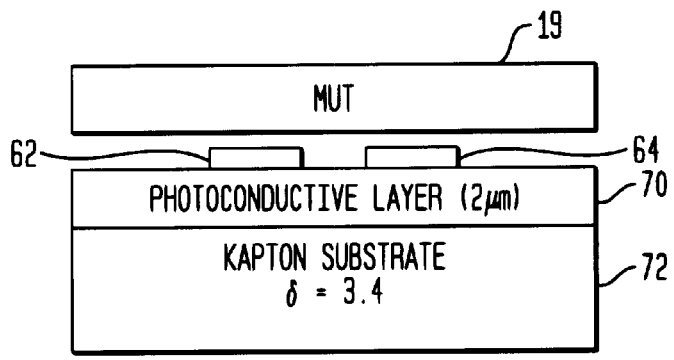
FIGS. 5a, 5b and 5c are views schematically showing the position of the waveguide and material under test (MUT) during measurements.
Figure 5B:
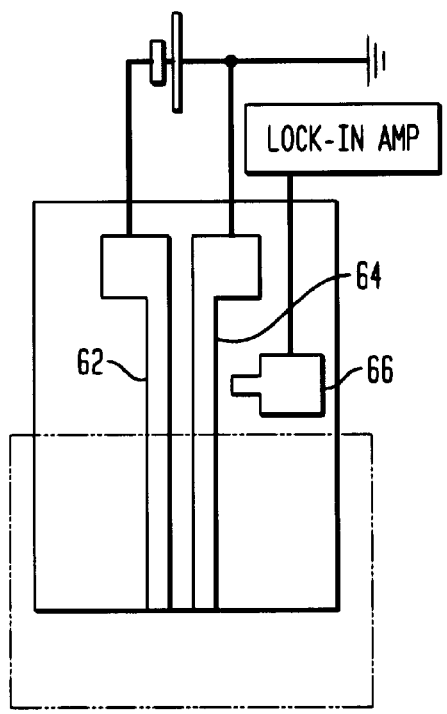
Figure 5C:
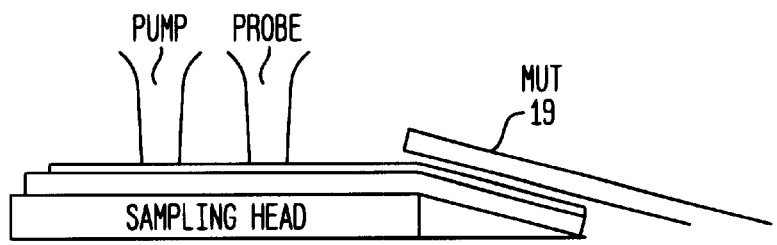
Figure 5D:
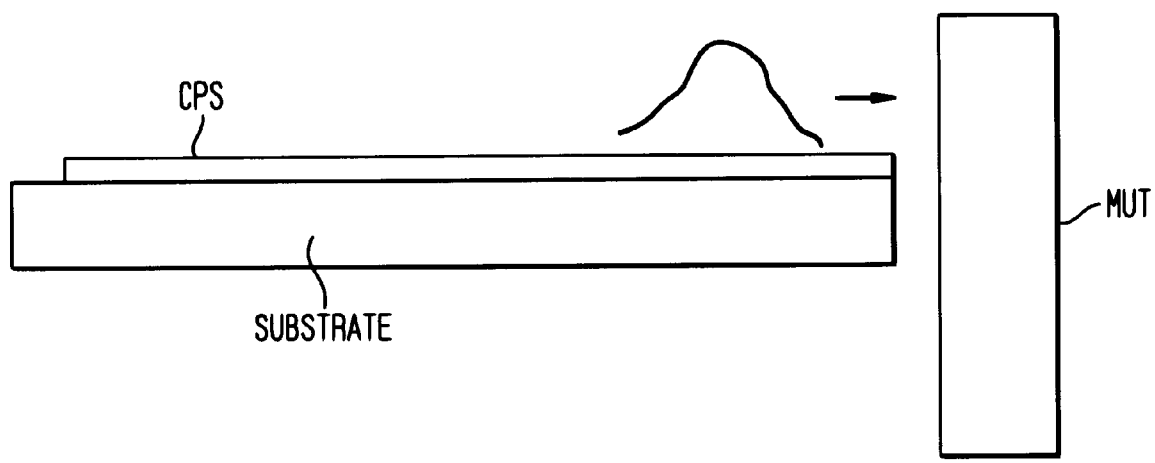
FIGS. 5d and 5e depict alternative placement of the MUT relative to the waveguide.
Figure 5E:
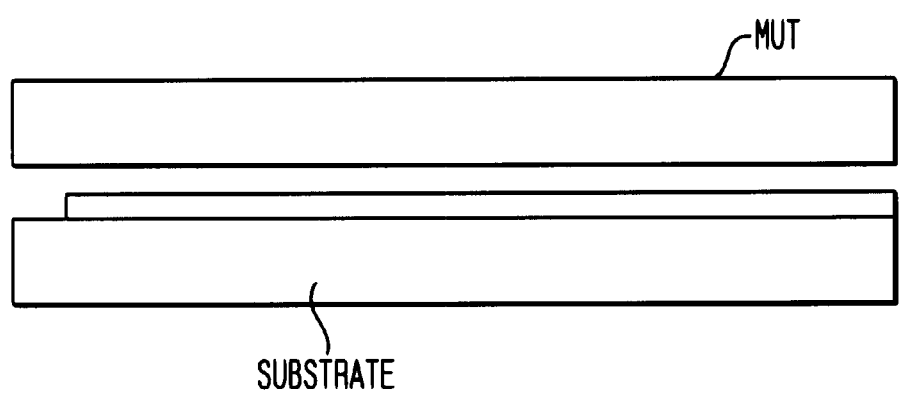

With the foregoing development of waveguide propagation principles, the method and structure of the invention can now be described in more detail. That discussion will be centered on FIGS. 5a, 5b and 5c along with FIGS. 5d and 5e. FIGS. 5a, 5b and 5c schematically depict, respectively, an end view, a top view and a side view of a sampling head used to carry out the method of the invention, along with an illustrative MUT juxtaposed relative to the sampling head in a preferred position. FIGS. 5d and 5e depict alternative placement of the MUT relative to the sampling head. Reference is also made back to FIG. 1a for an overall perspective of a system for exciting the sampling head and providing the associated sampling signal.

As noted in the earlier discussion of FIG. 1, the invention operates to detect and interpret an interaction between a GHz-Thz pulsed electric field and an MUT, to measure parameters of interest for the MUT. In particular, the pulsed electric field is propagated in a waveguide and excited by a pulsed laser source. This approach has been chosen by the inventors because a purely electronic arrangement would not be fast enough to generate and detect pulses at the frequency needed. A coplanar stripline waveguide deposited on a photoconducting substrate with sufficiently short generated carrier lifetime provides an effective mechanism for generating and detecting the pulsed electric field needed for the measurement methodology of the invention.

When the Pump pulse strikes an area between the biased coplanar transmission lines of the CPS (such as point 60 of FIG. 2*a*), it generates an electrical pulse—effectively translating the optical pulse into an electrical pulse—that propagates down the transmission line. When a sampling pulse strikes the Probe gap of the sampling head, a small amount of charge is transferred from the CPS line to the sampling line. The amount of charge transferred is proportional to the electric field at that point, and provides a measure of the electric field. A key aspect of the methodology of the invention is that one can delay when the probe pulse samples the field relative to the time of the pump pulse exciting the waveguide. Basically, one can then see the pulse propagate down the line. By scanning delay and monitoring the sampling line, one can easily time-resolve pulse propagation on the line. This allows one to extract waveguide parameters as expressed in equations 2 and 3, and thereby obtain properties of the MUT.

In one embodiment of the invention, the MUT is placed at the end of the waveguide (as illustrated in FIG. 5*d*), pulses are caused to propagate down the waveguide and the change in the reflected pulse due to the presence of the MUT is measured. However, it has been found empirically that highly precise positioning of the MUT at the end of the waveguide is required to obtain useful measurement results. Because the state of the current art in mechanisms for so positioning the MUT make such highly precise positioning somewhat problematical, other measurement embodiments are presently considered more desirable.

A first preferred embodiment contemplates the placement of the MUT parallel to the plane of the coplanar transmission lines and disposed in close proximity to the transmission lines. This embodiment is illustrated in FIG. 5*e*. In this position, the MUT can be viewed as a superstrate for the CPS of the sampling head. For this embodiment, adequate measurement accuracy is achieved, but spacial resolution for the measurement is reduced relative to placement of the MUT at the end of the waveguide—i.e., the MUT covers the entire waveguide so that properties of the MUT are measured over a 5–10 mm section of the waveguide.

The most preferred placement of the MUT relative to the sampling head is illustrated in FIGS. 5*a*, 5*b* and 5*c*, and is related to another property of the CPS embodied in the sampling head. At high frequency, if the dielectric constant of the substrate is high compared to air, then the electric field enters a non-TEM mode, where most of the field is in the substrate. For GaAs, a commonly used compound for photoconducting devices, the dielectric constant in 13, which is high enough to be troublesome in respect to the property described above. Thus with a GaAs photoconductor, only a very small electric field will exist above the transmission lines, with the result that the MUT has to be very close (a few microns) away from the metal strip lines in order to get useful measurements of MUT properties.

The inventors solved this problem by transferring the photoconductive layer onto a new, low dielectric constant polyimide substrate (Kapton: dielectric constant=3.4). With this change, MUTs can be brought to within 50 microns of the waveguide surface and still obtain useful measurement results.

The choice of a Kapton substrate for the CPS of the sampling head provides another advantage. Because Kapton is flexible it became possible to bend the waveguides without losing functionality for the transmission line beyond the bend transition. This enabled the inventors to overcome the lack of spacial resolution experienced with the previously described embodiment.

By configuring the waveguide as shown particularly in FIG. 5*c*, with an angled section at the end of the waveguide, the MUT can be positioned for measurement adjacent to the angled portion of the waveguide. With this configuration, smaller portions of the MUT can be measured, thus considerably improving spatial resolution for the measurement process.

As already indicated, the sampling head in the preferred embodiment is implemented with a CPS deposited on a photoconducting substrate. Preferably the sampling head will be characterized by the following design paramenters:

- the waveguide should be formed by highly conductive metal lines (for example, gold);
- the photoconductive layer underneath the metal lines should be made as thin as possible (for example, 2 μm thin low temperature grown GaAs); and
- the substrate 72 should be made of a material which does not absorb electromagnetic waves in the GHz-THz region, and with the refractive index as close to unity as possible (for example, glass, 50 μm kapton or other plastic film).

Such a sampling head can be constructed in the following manner. A thin layer of low-temperature GaAs is grown by Molecular Beam Epitaxy on a GaAs substrate, with an underlying layer of AlGaAs. The structure is then epoxied to a thin piece of polyimide (Kapton). The GaAs substrate is then etched away, with the AlGaAs acting as an etch-stop. The AlGaAs is then etched off, leaving the thin layer of low-temperature GaAs (70 in FIG. 5*a*) epoxied to the polyimide (72 in FIG. 5*a*). Metallic coplanar strip transmission lines (62 and 64 in FIG. 5*a*) are deposited on the GaAs, with suitable gaps for excitation by a pulsed laser.

The inventors have experimentally evaluated various embodiments of the invention, and describe results of that evaluation hereafter. Data was obtained using the arrangement where the MUT was used as a superstrate placed a few micrometers above the coplanar waveguides 62 and 64 as shown in FIGS. 5*a*, 5*b*, and 5*c*. Note that the sampling head is indicated at 66 of FIG. 5*b*. In this case, the electric field that extends into the air interacts with the MUT 19 on its way to the end of the coplanar lines and back. The advantage here is not only a stronger signal, because the length of interaction defines the signal strength, but more importantly, the signal emerges between the reference and reflected peaks, which makes the task of differentiation of signals much easier.

Figure 6A:
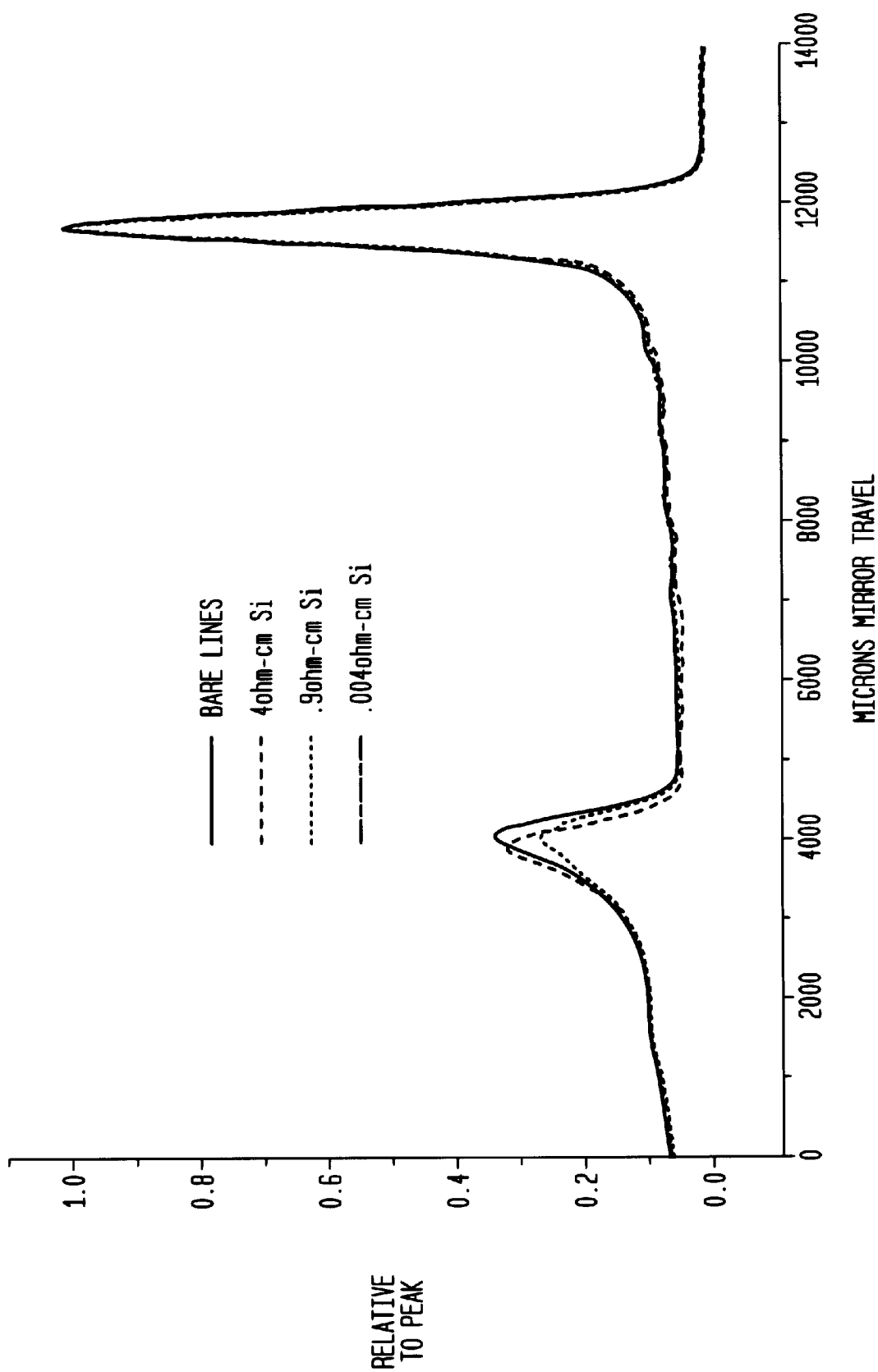
Figure 6B:
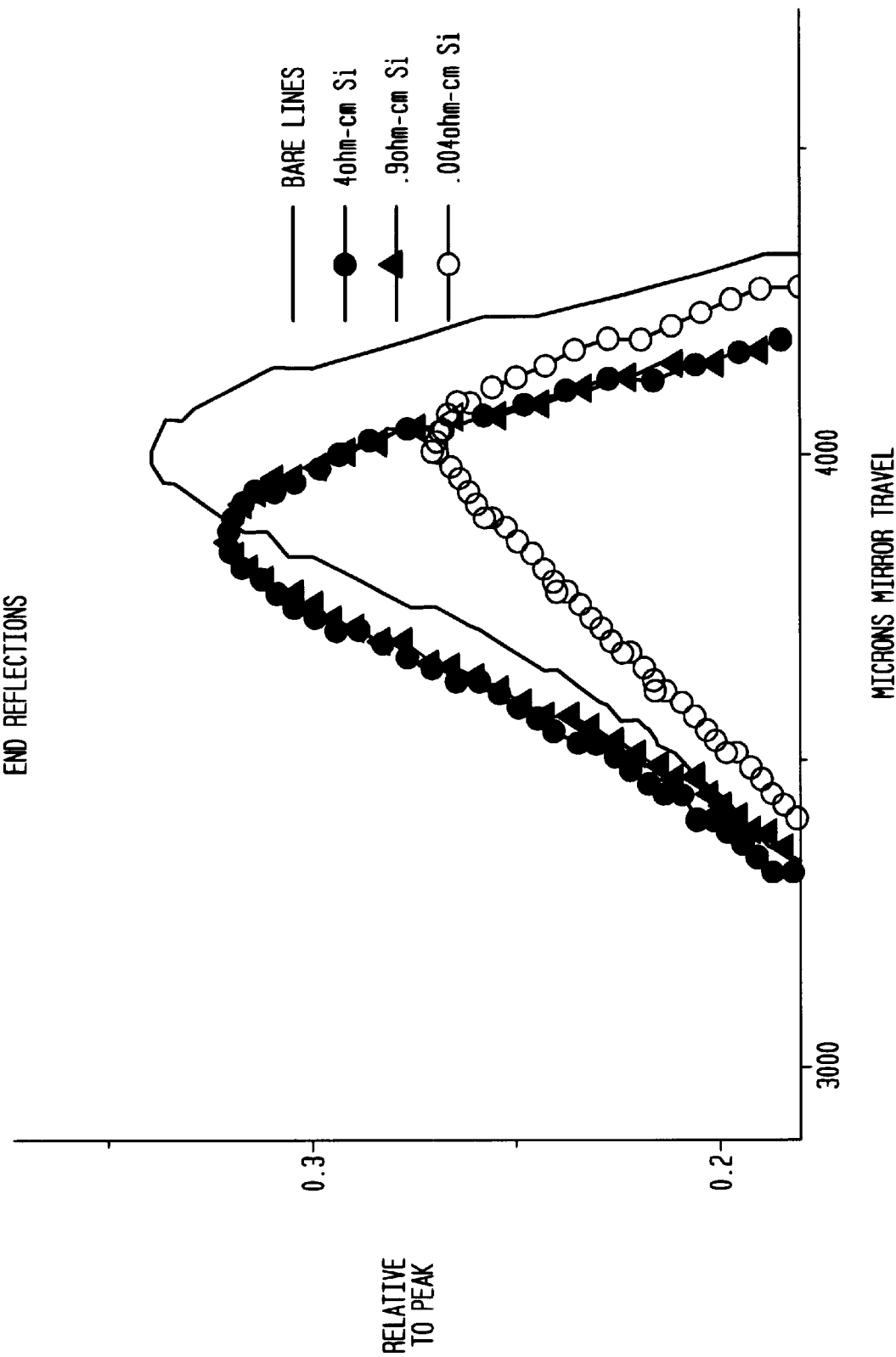
Figure 7:
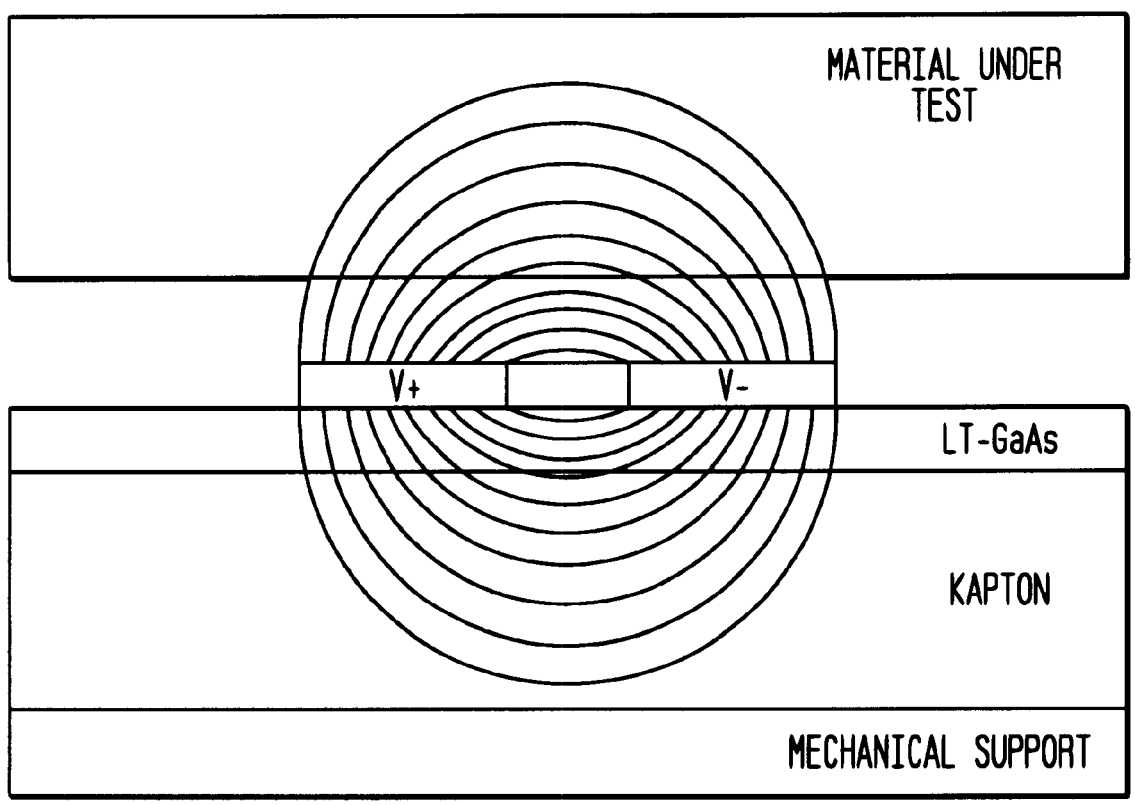
FIG. 7 is a field distribution between the sampling head and the MUT in the case of a dielectric wafer.
Figure 8:
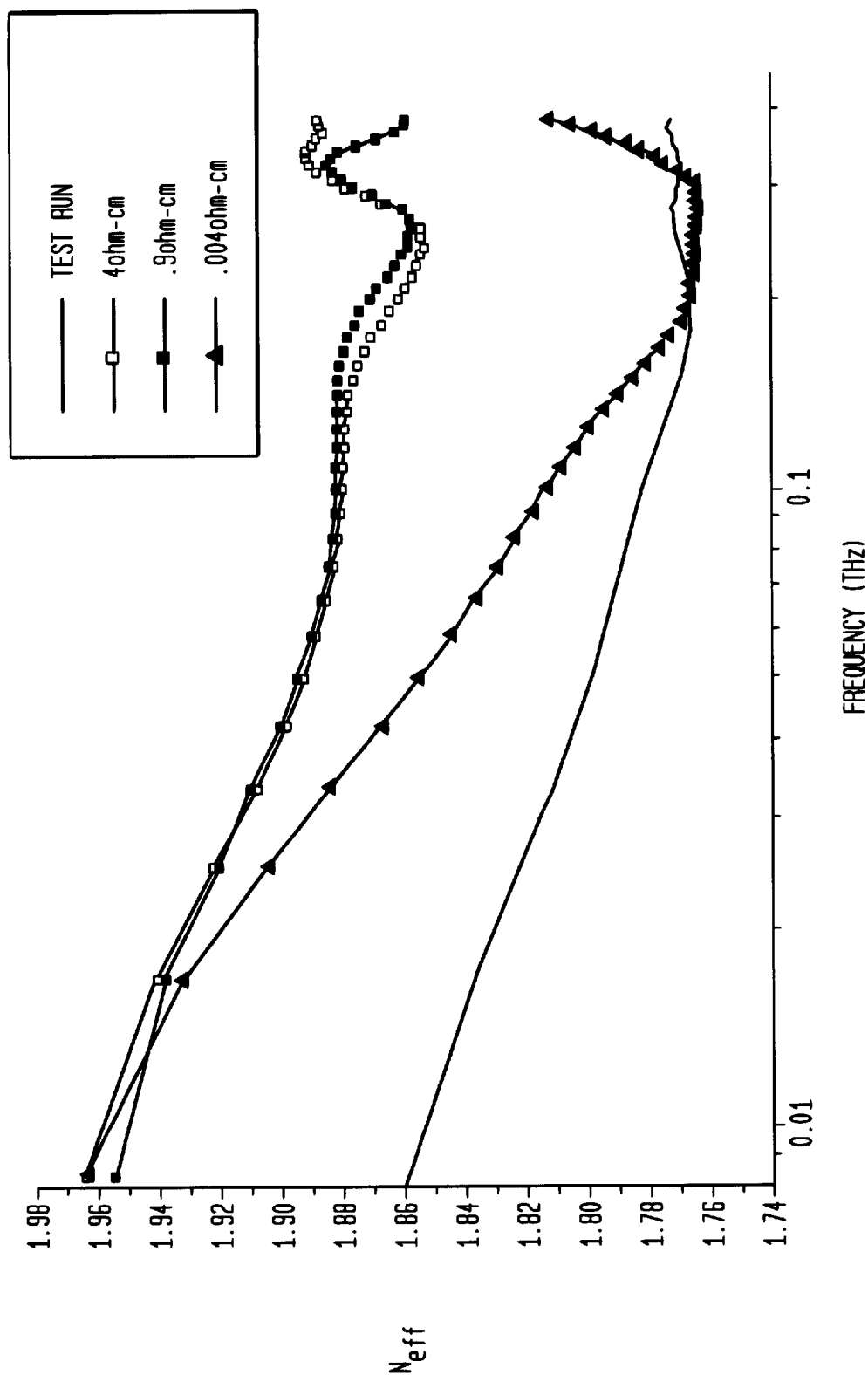
FIG. 8 is a graph of frequency dependence of the effective refractive index of coplanar stripline, and three Si wafers with different concentration of impurities.
Figure 9:
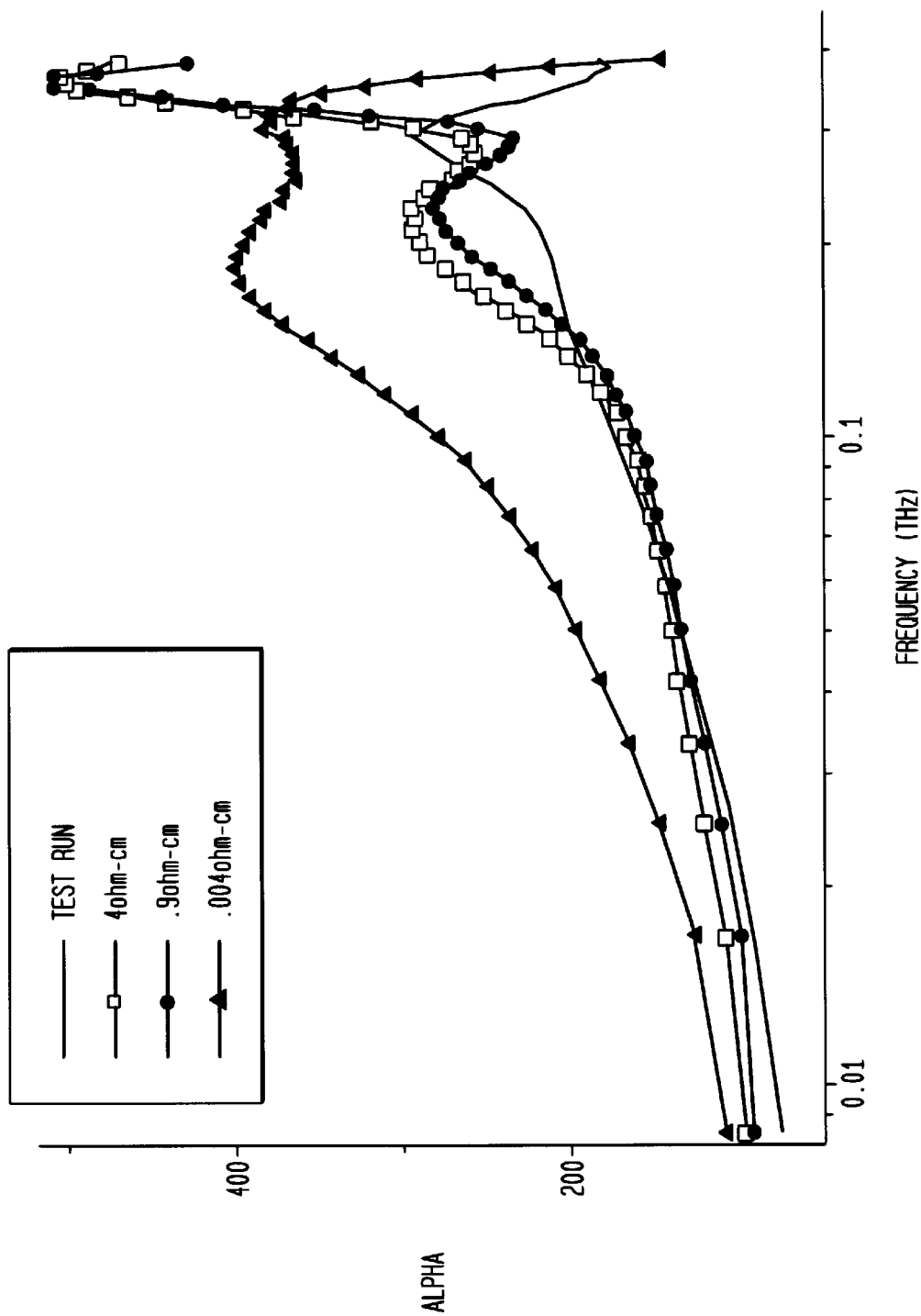
FIG. 9 is a graph of frequency dependence of the effective attenuation in coplanar stripline, and three Si wafers with different concentration of impurities.

FIGS. 6*a*, 6*b* and 6*c* show typical data scans recorded with doped Si wafers. The overall relationship between the reference and reflected peaks for various conductivities of the MUT, and the case of no MUT (indicated as "Bare Lines"), is shown in FIG. 6*a* for perspective. FIGS. 6*b* and 6*c* then provide a larger scale view of the reflected and reference curves, respectively. Two features are noteworthy here. First, the intensity of the reflected peak depends strongly upon wafer conductivity, i.e. doping. Second, the delay of the reflected peak with respect to the reference peak is also a function of wafer conductivity. In the case of propagation of the pulse when a lightly doped Si wafer is measured, a substantial fraction of the field propagates inside the wafer, as schematically illustrated in FIG. 7. The velocity of light in Si is slower than in air, therefore it takes the pulse more time to travel, and it arrives to the sampling gap later than in the case when there is no MUT. When the doping level of the MUT increases, pushing the plasma frequency above the measurement frequency, only a small fraction of the field (measured by the skin depth) can penetrate into the MUT—most of the field propagates in the air gap between the sampling head and MUT. Therefore one should expect that the reflected peak will arrive at the sampling gap with almost no delay with respect to the reference pulse. This indeed was observed on the Si wafer with 0.004 Ωcm as shown on FIG. 6b. In order to use equations 2 and 3, the reference and reflected peaks were truncated and Fourier transformed; after that $\alpha(\omega)$ and $n(\omega)$ were obtained from (2) and (3). The results are shown on FIGS. 8 and 9.

For heavily doped semiconductors and metals the quantitative analysis is becoming very complicated because the pulse does not propagate as a quasi-TEM mode any more, but rather as two coupled micro-strip modes. In this case other embodiments of the sampling head, such as microstrip (illustrated schematically in FIG. 14a), may be more useful.

Figure 10A:
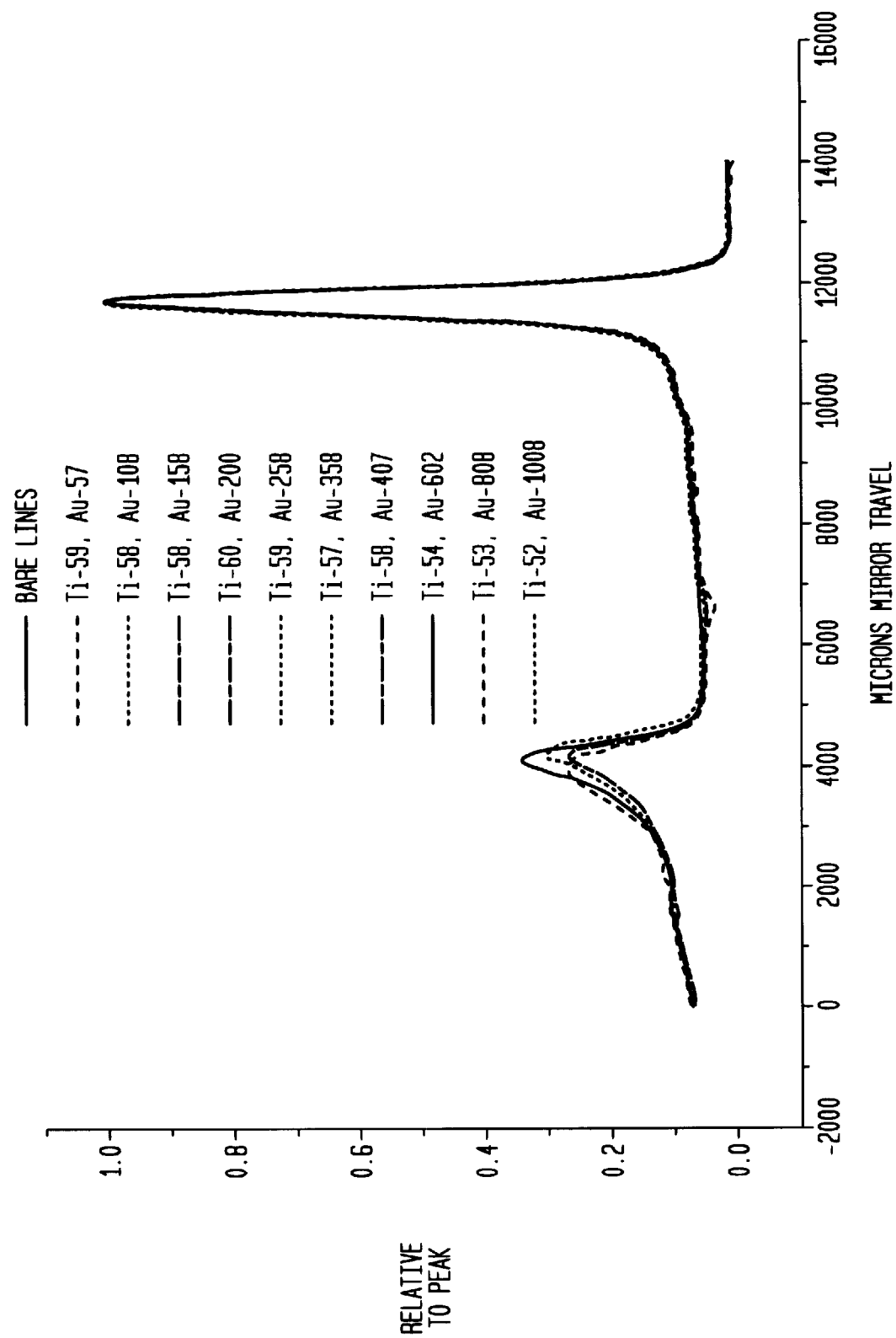
FIGS. 10a, 10b and 10c provide a graph, and a scaled-up portion of the graph, of time-domain spectra taken for a set of Ti/Au samples with different thickness of the gold layer.
Figure 10B:
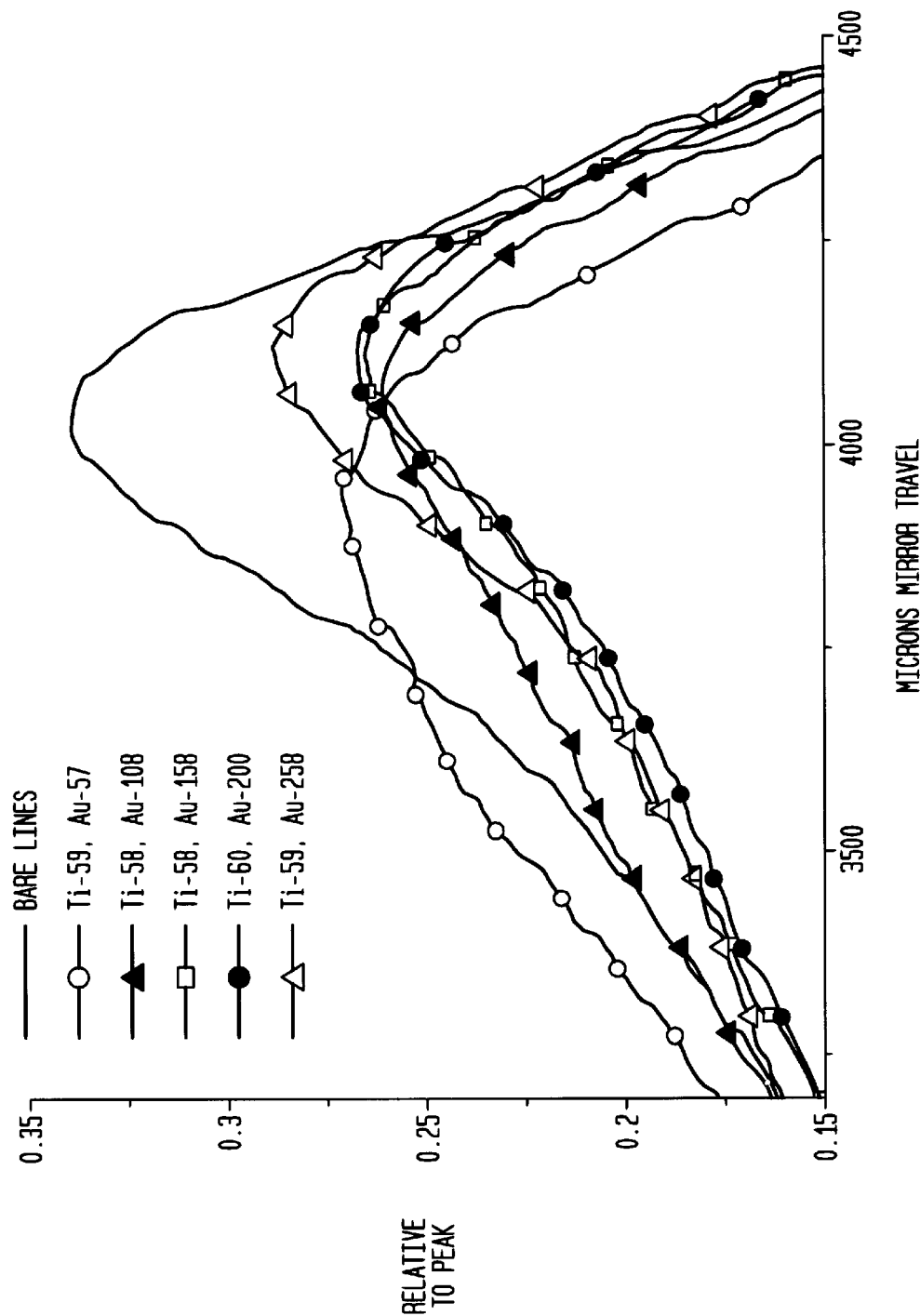
Figure 10C:
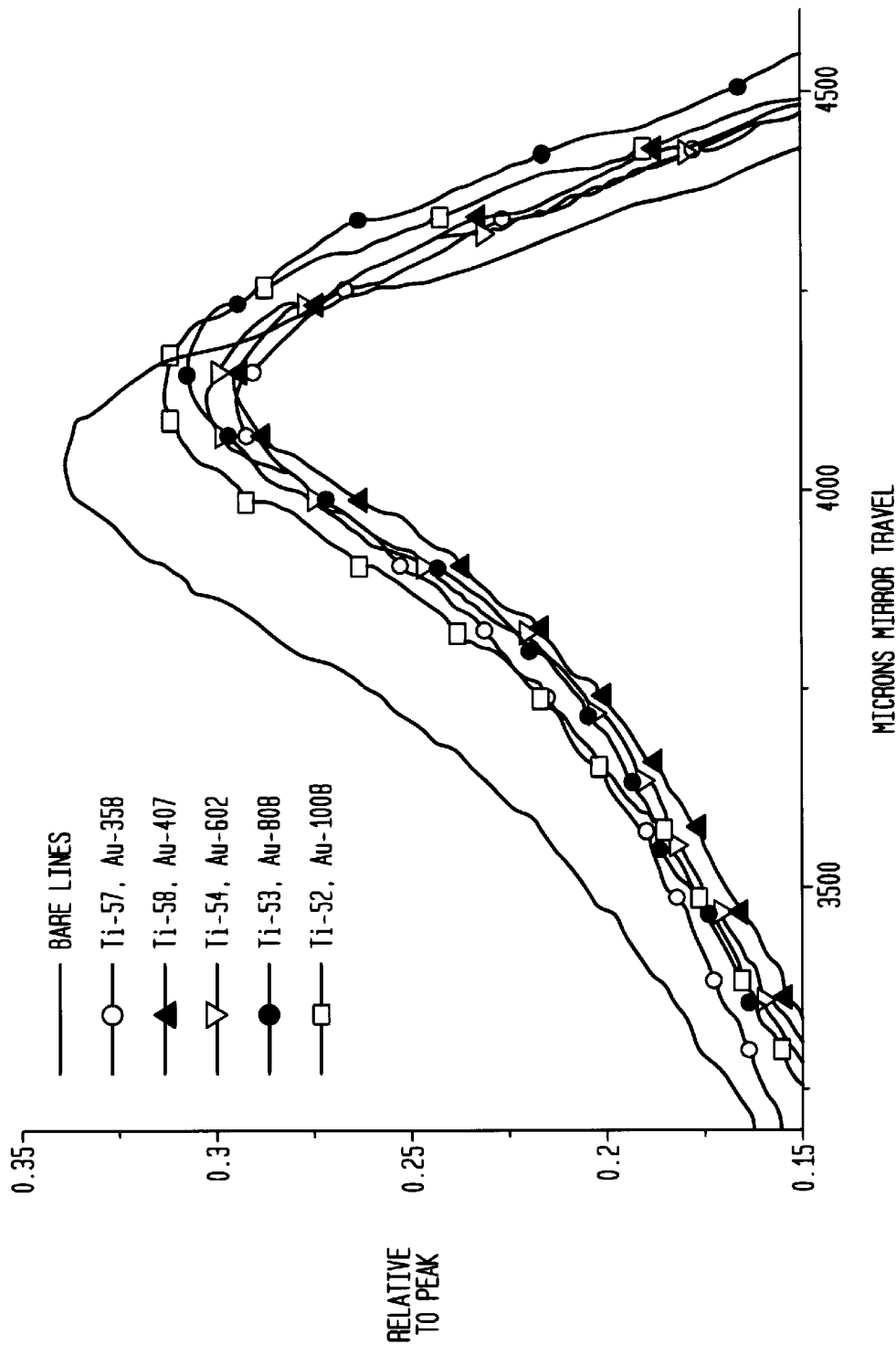

FIGS. 10a, 10b and 10c show the results of measurements performed on a set of wafers with different thickness of the metal used to form the coplanar transmission lines. In particular, FIG. 10a shows the overall relationship between the reference and reflected peaks for various thicknesses, and then the curves are divided into two parts (to improve intelligibility) and a larger scale scale view of the reflected curves for each set is shown in FIGS. 10b and 10c. One can clearly see from these figures that just 50 Angstrom difference in the thickness of the gold layer causes detectable changes in the shape of the reflected pulse. It should also be noted that information about the wafer under testing is included in the phase and the attenuation of the reflected signal.

Figure 12:
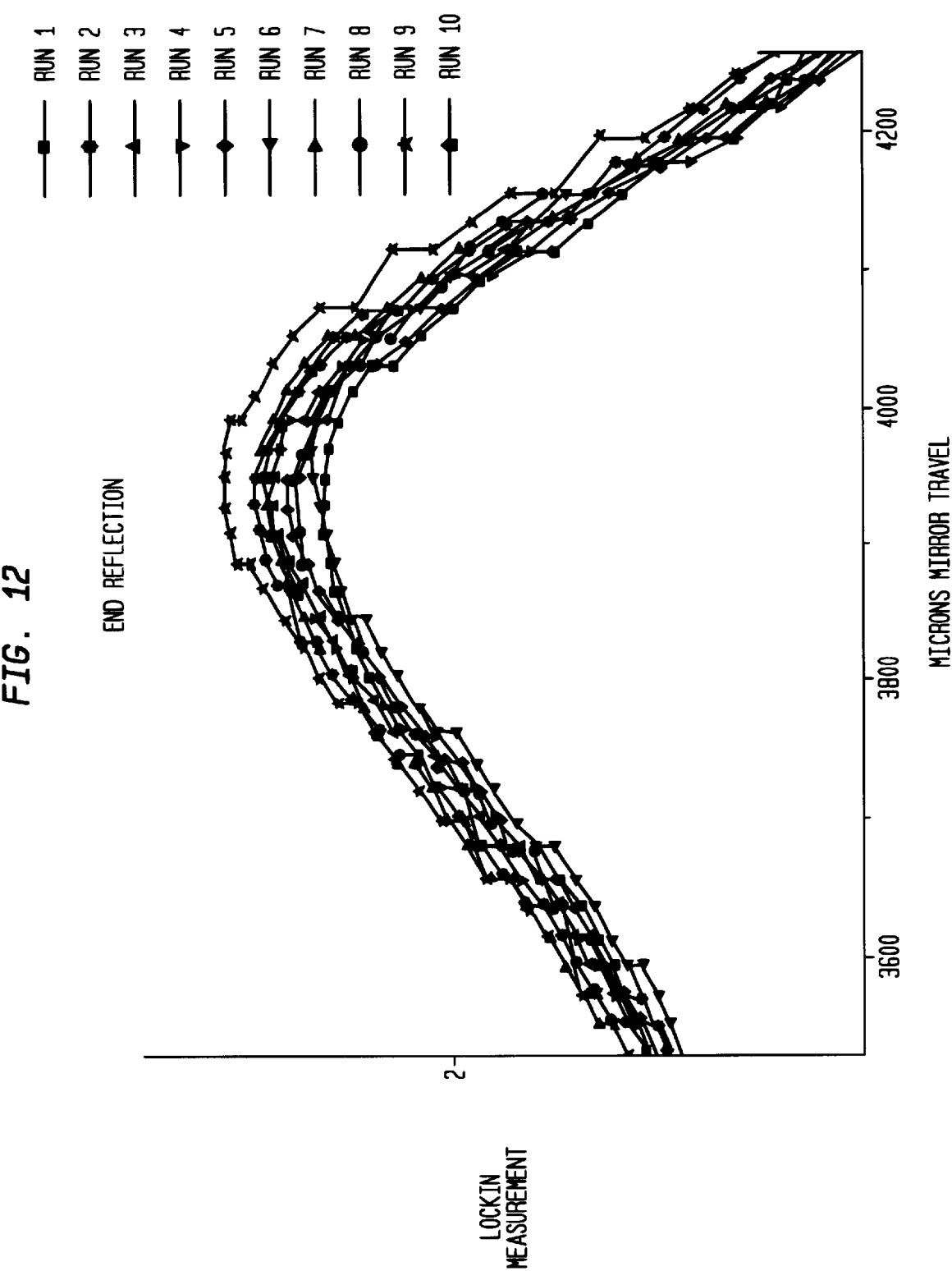
FIG. 12 is a graph showing the changes in amplitude and position of the reflected peak during static repeatability test.

In order to evaluate static repeatability, ten measurements of the same sample were taken sequentially, without any changes in the position of the MUT and sampling head, nor in the alignment of the laser beams onto launching and sampling gaps. The results are shown on the FIGS. 11 and 12 for the initial pulse and reflected one, respectively. The major source of instability during this experiment was the Ar laser, which affected the intensity of both initial and reflected pulses. Another source of error is the synchronization of the data acquisition system and the delay stage, which manifests itself in step-like features on the curves. Despite these difficulties the standard deviations of the pulse intensity were 2.1% and 2.7% for initial and reflected pulses, respectively. These numbers can be improved at least an order of magnitude, provided a quieter laser source and higher modulation frequency are used.

Estimates of sensitivity were made using the data presented in FIG. 10. For the Ti/Au system, a 50 Angstrom change in the thickness of gold layer increases the amplitude of the reflected peak by 2% for very thin Au films (<250 Angstrom). It takes about 200 Angstrom to produce comparable changes when the Au film thickness lies in the 1000 Angstrom range.

Semiconductor and metal film resistivity comprise an electrical property of a material. As such, the non-contact GHz-THz probe of the present invention represents a viable alternative to the currently employed 4-point probes, and is competitive with other proposed non-contact resistivity measurement techniques. The probe method is based on well-established physical principles. Finite element based modeling software, which is well-developed and commercially available, can be used to extract accurate material parameters. The systematic approach to engineering, as a part of the development of a commercial tool should easily improve the accuracy, sensitivity, and repeatability of the measurements to the level expected in semiconductor metrology.

Figure 13:
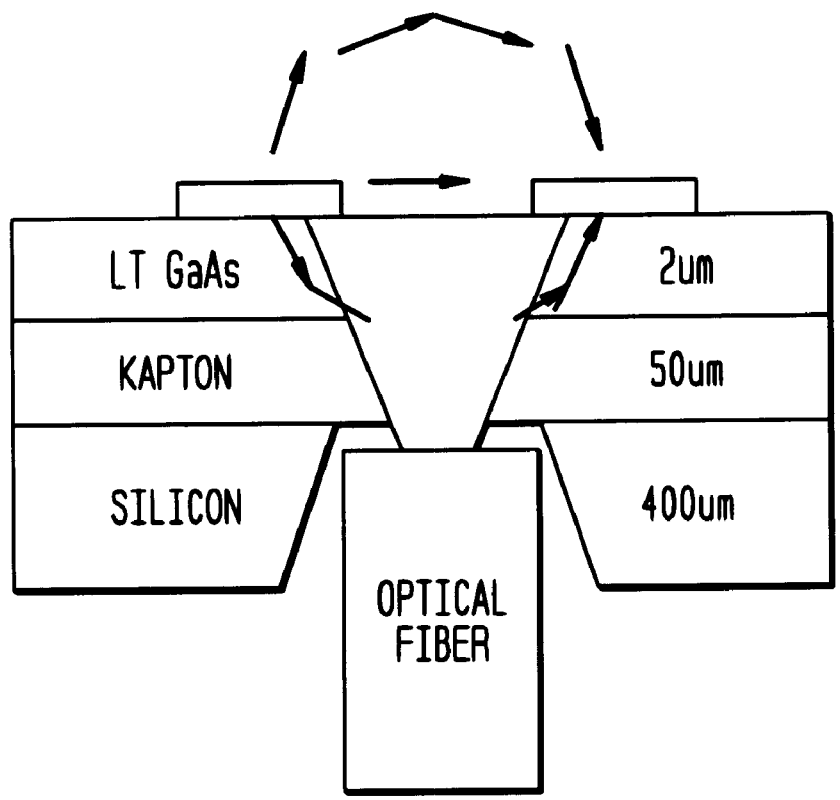
FIG. 13 shows another embodiment of the sampling head of the invention.

Another embodiment of the invention is shown in FIG. 13, where the laser pulses for excitation and sampling of the waveguide are provided to the sampling head via a fiber optic cable, rather than though a free-space path. Although the physical principles and basic methodology are the same as for the embodiments previously discussed involving a free-space path for the laser pulses, it is believed that this embodiment may be more suitable for commercial development.

In yet another embodiment, two sampling gaps can be utilized to allow for the observation of the signal as it travels along the waveguide. By sampling the signal at two points, the dispersion of the waveguide can be calculated.

Figure 14A:
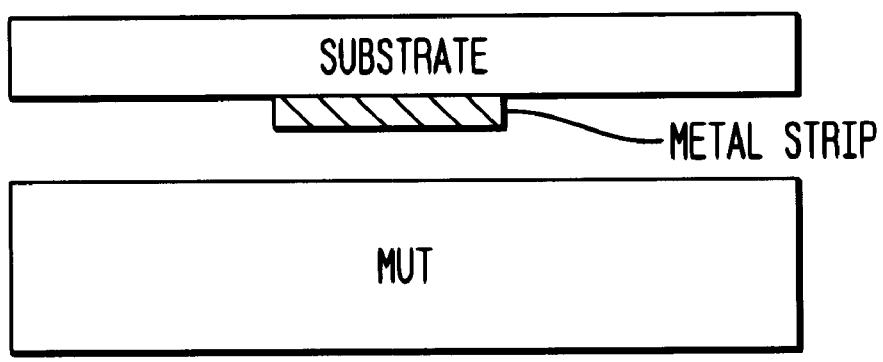
FIG. 14 shows additional embodiments for sampling head of the invention.
Figure 14B:
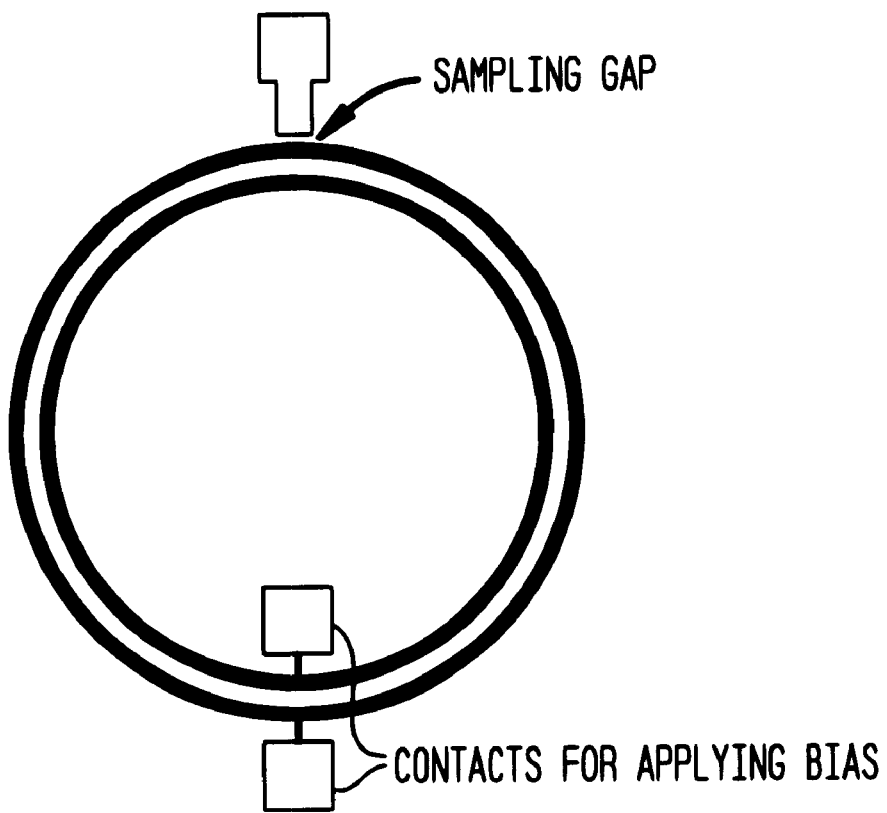
Figure 14C:
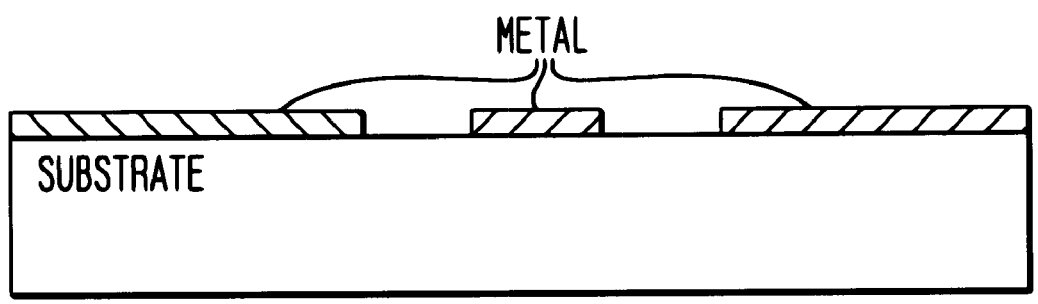

In a still further embodiment of the invention, schematically illustrated in FIG. 14a, the sampling head can be implemented as a microstrip (i.e single transmission line) deposited on a photoconducting substrate. However, because substantially all of the electric field generated in the microstrip propagates downward into the substrate, it is necessary to place the MUT in the position of the ground plane for the microstrip. Because the MUT acts as the ground plane for the microstrip, it should be a highly doped semiconductors sample or a metal film. With this modification of the structure previously described for a the CPS embodiment, the method of the invention would otherwise be carried out in a corresponding manner to that described for the CPS embodiment. Other embodiments of the sampling head of the invention, specifically, a two conductor ring waveguide using one sampling gap and the Coplanar Waveguide (CPW), are shown schematically in FIGS. 14b and 14c for completeness as they may provide increased sensitivity.

Although the preceding discussion has been focused on the measurement of electrical properties of materials, as the preferred embodiment of the invention, it should be noted that a probe established in the manner of the invention is expected to also be sensitive to other material properties such as strain or magnetic permeability. Such applications are intended to be within the scope of the invention as claimed hereafter.

Having thus described the invention in detail, it is to be understood that the foregoing description is not intended to limit the spirit and scope thereof. What is desired to be protected by Letters Patent is set forth in the appended claims.

What is claimed is:

1. An apparatus for non-destructive measurement of electrical properties of materials comprising:

a pulsed light source and means for providing light pulses therefrom to prescribed locations;

an electro-optical device operable to convert optical pulses from said pulsed light source into electrical pulses;

a guided wave structure operable to receive said electrical pulses and to cause said pulses to propagate from a point of generation to at least one sampling position; and a sampling device implemented as a semiconductor device for sampling a field of said electrical pulse at said sampling location;

wherein a material under test (MUT) is positioned in proximity to said guided wave structure in a manner to interact with said electrical pulse field.

2. The apparatus of claim 1, wherein said optical pulses and said electrical pulses derived therefrom are characterized by GigaHertz bandwidth.

3. The apparatus of claim 1, wherein said optical pulses and said electrical pulses derived therefrom are characterized by TeraHertz bandwidth.

4. The apparatus of claim 1, wherein said means for providing light pulses to prescribed locations is free-space based, and further comprises:
 one or more focusing elements; and
 means for positioning an output of said one or more focusing elements at a desired impingement point.

5. The apparatus of claim 1, wherein said means for providing light pulses to prescribed locations is fiber-optics based, and further comprises:
 a pulsed light to fiber coupler; and
 one or more fiber positioning elements.

6. The apparatus of claim 1, wherein said electro-optical device is comprised of a photoconductor.

7. The apparatus of claim 6, wherein said photoconductor is comprised of a semiconductor material.

8. The apparatus of claim 1, wherein said electro-optical device causes a unipolar electrical pulse to be generated in response to said light pulse.

9. The apparatus of claim 1, wherein said electro-optical device causes a bi-polar electrical pulse to be generated in response to said light pulse.

10. The apparatus of claim 1, wherein said electro-optical device is incorporated into said guided wave structure.

11. The apparatus of claim 1, wherein said electro-optical device is separate from said guided wave structure.

12. The apparatus of claim 11, wherein said electro-optical device is coupled to said guided wave structure through flip-chip bonding.

13. The apparatus of claim 11, wherein said electro-optical device is coupled to the guided waive structure through capacitive coupling.

14. The apparatus of claim 1, wherein said sampling device is incorporated into said guided wave structure.

15. The apparatus of claim 1, wherein said sampling device is an Auston switch.

16. The apparatus of claim 1, wherein said sampling device is separate from said guided wave structure.

17. The apparatus of claim 1, wherein said sampling device is an external electro-optic probe.

18. The apparatus of claim 1, wherein said guided wave structure is comprised of conducting lines on a photoconductive layer.

19. The apparatus of claim 18, wherein said photoconductive layer comprises Low Temperature GaAs (LT-GaAs).

20. The apparatus of claim 18, wherein said guided wave structure further comprises a substrate supporting said photoconductive layer.

21. The apparatus of claim 20, wherein said photoconductive layer and said substrate are flexible.

22. The apparatus of claim 20, wherein said substrate is comprised of multiple layers.

23. The apparatus of claim 20, wherein said substrate contains apertures in which optical fibers are fixed to deliver light to prescribed locations.

24. The apparatus of claim 18, wherein said electro-optical device and said sampling device are fabricated from said photoconductive layer.

25. An apparatus for non-destructive measurement of electrical properties of materials comprising:
 a pulsed light source and means for providing light pulses therefrom to prescribed locations;
 an electro-optical device operable to convert optical pulses from said pulsed light source into electrical pulses;
 a guided wave structure operable to receive said electrical pulses and to cause said pulses to propagate from a point of generation to at least one sampling position, said guided wave structure comprising conducting lines on a photoconductive layer; and
 a sampling device for sampling a field of said electrical pulse at said sampling location;
 wherein a material under test (MUT) is positioned in proximity to said guided wave structure in a manner to interact with said electrical pulse field.

26. The apparatus of claim 25, wherein said optical pulses and said electrical pulses derived therefrom are characterized by GigaHertz bandwidth.

27. The apparatus of claim 25, wherein said optical pulses and said electrical pulses derived therefrom are characterized by TeraHertz bandwidth.

28. The apparatus of claim 25, wherein said means for providing light pulses to prescribed locations is free-space based, and further comprises:
 one or more focusing elements; and
 means for positioning an output of said one or more focusing elements at a desired impingement point.

29. The apparatus of claim 25, wherein said means for providing light pulses to prescribed locations is fiber-optics based, and further comprises:
 a pulsed light to fiber coupler; and
 one or more fiber positioning elements.

30. The apparatus of claim 25, wherein said electro-optical device is comprised of a photoconductor.

31. The apparatus of claim 30, wherein said photoconductor is comprised of a semiconductor material.

32. The apparatus of claim 25, wherein said electro-optical device causes a unipolar electrical pulse to be generated in response to said light pulse.

33. The apparatus of claim 25, wherein said electro-optical device causes a bi-polar electrical pulse to be generated in response to said light pulse.

34. The apparatus of claim 25, wherein said electro-optical device is incorporated into said guided wave structure.

35. The apparatus of claim 25, wherein said electro-optical device is separate from said guided wave structure.

36. The apparatus of claim 35, wherein said electro-optical device is coupled to the guided wave structure through flip-chip bonding.

37. The apparatus of claim 35, wherein said electro-optical device is coupled to the guided wave structure through capacitive bonding.

38. The apparatus of claim 25, wherein said sampling device is incorporated into said guided wave structure.

39. The apparatus of claim 25, wherein said sampling device is an Auston switch.

40. The apparatus of claim 25, wherein said sampling device is separate from said guided wave structure.

41. The apparatus of claim 25, wherein said sampling device is an external electro-optic probe.

42. The apparatus of claim 25, wherein said photoconductive layer comprises Low Temperature GaAs (LT-GaAs).

43. The apparatus of claim 25, wherein said guided wave structure further comprises a substrate supporting said photoconductive layer.

44. The apparatus of claim 43, wherein said photoconductive layer and said substrate are flexible.

45. The apparatus of claim 43, wherein said substrate is comprised of multiple layers.

46. The apparatus of claim 43, wherein said substrate contains apertures in which optical fibers are fixed to deliver light to prescribed locations.

47. The apparatus of claim 25, wherein said electro-optical device and said sampling device are fabricated from said photoconductive layer.

48. A method for non-destructive measurement of electrical properties of materials comprising:

provinding light pulses from a pulsed light source to an electro-optical device operable to convert optical pulses from said pulsed light source into electrical pulses;

providing said converted electrical pulses to a guided wave structure operable to cause said electrical pulses to propagate from a point of generation to at least one sampling position, said guided wave structure comprised of conducting lines on a photoconductive layer;

positioning a material under test (MUT) in proximity to said guided wave structure; and sampling a field of said electrical pulse at a point in said guided wave structure.

49. The method of claim 48, wherein said optical pulses and said electrical pulses derived therefrom are characterized by GigaHertz bandwidth.

50. The method of claim 48, wherein said optical pulses and said electrical pulses derived therefrom are characterized by TeraHertz bandwidth.

51. The method of claim 48, wherein said electro-optical device is implemented as a photoconductor.

52. The method of claim 48, wherein said electro-optical device causes a unipolar electrical pulse to be generated in response to said light pulse.

53. The method of claim 48, wherein said electro-optical device causes a bi-polar electrical pulse to be generated in response to said light pulse.

* * * * *